United States Patent
Karch et al.

(10) Patent No.: US 9,695,201 B2
(45) Date of Patent: *Jul. 4, 2017

(54) PROCESS FOR PREPARING TRIALKYL COMPOUNDS OF METALS OF GROUP IIIA

(71) Applicant: Umicore AG. & Co. KG, Hanau (DE)

(72) Inventors: Ralf Karch, Kleinostheim (DE); Andreas Rivas-Nass, Schriesheim (DE); Annika Frey, Hanau (DE); Tobias Burkert, Murr (DE); Eileen Woerner, Nidderau (DE); Angelino Doppiu, Seligenstadt (DE)

(73) Assignee: UMICORE AG & CO. KG, Hanau (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/358,069

(22) PCT Filed: Nov. 28, 2012

(86) PCT No.: PCT/EP2012/073771
§ 371 (c)(1),
(2) Date: May 14, 2014

(87) PCT Pub. No.: WO2013/083449
PCT Pub. Date: Jun. 13, 2013

(65) Prior Publication Data
US 2014/0287141 A1    Sep. 25, 2014

(30) Foreign Application Priority Data
Nov. 28, 2011 (DE) .......... 10 2011 119 487
Jul. 16, 2012 (DE) .......... 10 2012 013 941

(51) Int. Cl.
| C07F 7/00 | (2006.01) |
| C23C 16/00 | (2006.01) |
| C07F 5/00 | (2006.01) |
| C23C 16/30 | (2006.01) |
| C23C 16/18 | (2006.01) |

(52) U.S. Cl.
CPC ........... *C07F 5/00* (2013.01); *C23C 16/18* (2013.01); *C23C 16/301* (2013.01); *Y02P 20/582* (2015.11)

(58) Field of Classification Search
CPC .................... C07F 5/00; C23C 16/18
USPC .......................... 427/252; 556/107
See application file for complete search history.

(56) References Cited

U.S. PATENT DOCUMENTS

| 3,318,931 A | 5/1967 | Dützer et al. |
| 5,043,462 A * | 8/1991 | Sundermeyer ........... C07F 5/00 556/1 |
| 5,350,869 A | 9/1994 | Kanjolia et al. |
| 5,473,090 A | 12/1995 | Smit et al. |
| 5,756,786 A | 5/1998 | Power et al. |
| 6,495,707 B1 | 12/2002 | Leese et al. |
| 7,166,734 B2 | 1/2007 | Shenai-Khatkhate et al. |
| 2002/0188145 A1* | 12/2002 | Shenai-Khatkhate .. C07F 9/723 556/64 |
| 2003/0191333 A1 | 10/2003 | Shenai-Khatkhate et al. |
| 2006/0047132 A1 | 3/2006 | Shenai-Khatkhate et al. |
| 2006/0075959 A1 | 4/2006 | Matsubara et al. |
| 2009/0054717 A1 | 2/2009 | Okada et al. |
| 2009/0149008 A1 | 6/2009 | Kryliouk et al. |
| 2014/0256974 A1 | 9/2014 | Karch et al. |

FOREIGN PATENT DOCUMENTS

| CN | 1872861 A | 12/2006 |
| CN | 1872862 A | 12/2006 |
| DE | 1158977 | 12/1963 |
| DE | 40 05 726 A1 | 10/1990 |
| EP | 1303336 | 4/2003 |

(Continued)

OTHER PUBLICATIONS

Gaines et al., "Trimethylgallium", Inorganic Syntheses, pp. 203-207.
J.J. Eisch et al, "Organometailic Compounds of Group III. I. The Preparation of Gallium and Indium Alkyls form Organoaluminum Compounds[18]", vol. 84, No. 19, pp. 3605-3610, Oct. 17, 1962.
Starowieyski et al., "Synthesis and purification of trimethylgallium for MOCVD: molecular structure of $(KF)_4 4\ (Me_3Ga)$", Applied Organometallic Chemistry, vol. 14, pp. 616-622, 2000.
International Search Report for PCT/EP2012/073771; mailed Mar. 25, 2013.
C. A. Kraus et al., "Trimethyl Gallium, Trimethyl Gallium Etherate and Trimethyl Gallium Ammine"; Chemistry: Kraus and Toonder, Proc. N. A. S.; 1933; pp. 292-298.

(Continued)

*Primary Examiner* — Sudhakar Katakam
*Assistant Examiner* — Kofi Adzamli
(74) *Attorney, Agent, or Firm* — Smith, Gambrell & Russell, LLP

(57) ABSTRACT

The invention relates to a process for preparing trialkylmetal compounds of the general formula $R_3M$ (where M=metal of group IIIA of the Periodic Table of the Elements (PTE), preferably gallium or indium, and R=$C_1$-$C_5$-alkyl, preferably methyl or ethyl).
The process is based on the reaction of metal trichloride ($MeCl_3$) with alkylaluminium sesquichloride ($R_3Al_2Cl_3$) in the presence of at least one alkali metal halide as auxiliary base. The reaction mixture is heated to a temperature above 120° C. and the trialkylmetal compound is separated off from the reaction mixture via a separator, with partially alkylated products being at the same time recirculated to the reaction mixture. In a further step, the reaction mixture is heated to a maximum of 350° C. and the remaining alkylated and partially alkylated products are separated off. The products obtained in this way can optionally be recycled in the process.
The process displays a high yield of trialkylmetal compound and also a high metal utilization; the products are used as precursors for MOCVD processes.

45 Claims, 1 Drawing Sheet

(56) References Cited

FOREIGN PATENT DOCUMENTS

| | | |
|---|---:|---|
| EP | 1489085 A1 | 12/2004 |
| EP | 1 643 547 A1 | 4/2006 |
| EP | 1 705 719 A1 | 9/2006 |
| JP | H02-295991 A | 12/1990 |
| JP | H08-501532 A | 2/1996 |
| JP | 2000-005503 A | 1/2000 |
| JP | 2002-533348 A | 10/2002 |
| JP | 2006-104189 A | 4/2006 |
| JP | 2006-265168 A | 10/2006 |
| JP | 2006-342101 A | 12/2006 |
| JP | 2009-067786 A | 4/2009 |
| JP | 2009-126835 A | 6/2009 |
| JP | 2010-195690 A | 9/2010 |
| WO | 00/37475 A1 | 6/2000 |
| WO | 02/07848 A1 | 1/2002 |
| WO | 2013/083449 A1 | 6/2013 |

OTHER PUBLICATIONS

D. F. Foster et al., "Electronic Grade Alkyls of Group 12 and 13 Elements"; Inorganic Syntheses, vol. 31, 1997, pp. 29-66.
L. I. Zakharkin et al., "A Simple Synthesis of Non-Solvated Trimethylgallium and Triethylgammium"; Synth. React. Inorg. Met.-Org., and Nano-Met. Chem, vol. 29 (7); (1999) 1243-1247.
Notification of Transmittal of the International Search Report and the Written Opinion for Application No. PCT/EP2012/073772 mailed Mar. 25, 2013.
Notification of Reasons for Refusal in JP 2014-542885 dated May 23, 2016 in Japanese with English Machine Translation (9 pages).
Search Report by Registered Searching Organization in JP 2014-542885 dated May 18, 2016 in Japanese with English machine translation (39 pages).
International Preliminary Report on Patentability for PCT/EP2012/073771 dated Jun. 3, 2014 (5 pages).

* cited by examiner

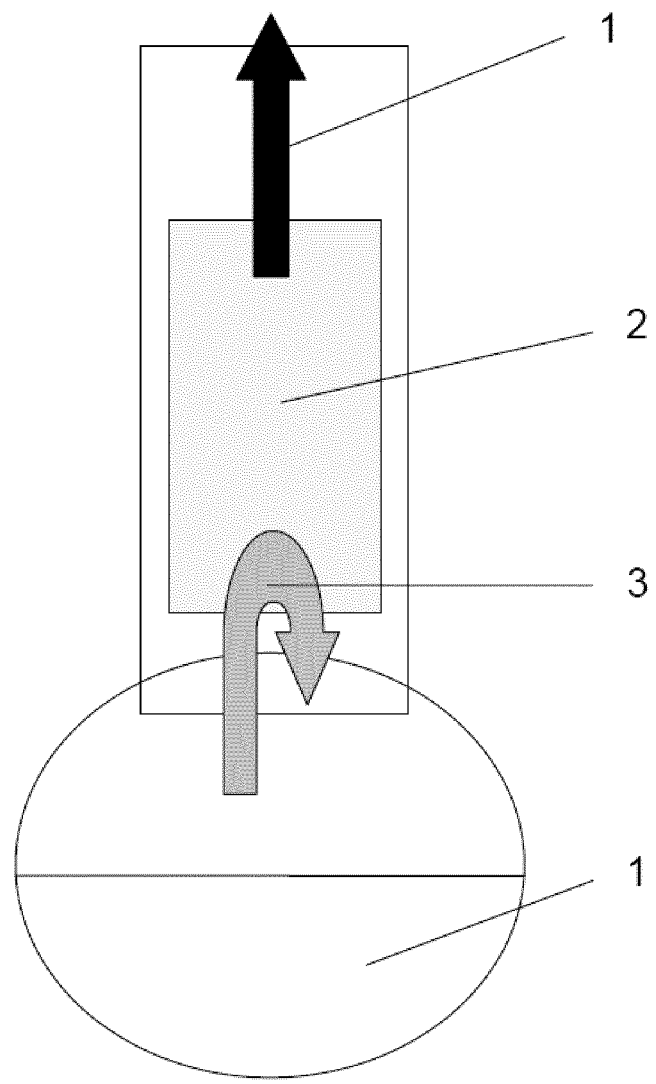

PROCESS FOR PREPARING TRIALKYL COMPOUNDS OF METALS OF GROUP IIIA

INTRODUCTION

The invention relates to a process for the inexpensive and environmentally friendly preparation of trialkyl compounds of metals of group IIIA of the Periodic Table. The compounds have the general formula $$R_3M$$

where M is a metal of group IIIA of the Periodic Table of the Elements (PTE), preferably gallium (Ga) or indium (In), and R is a $C_1$-$C_5$-alkyl group, preferably methyl or ethyl.

The process is based on the reaction of metal trichloride ($MCl_3$) with an alkylaluminium sesquichloride ($R_3Al_2Cl_3$) in the presence of at least one alkali metal halide as auxiliary base in a one-pot process. The reaction mixture is heated to a defined temperature and the trialkylmetal compound is separated off from the reaction mixture via a separator, with partially alkylated products simultaneously being recirculated to the reaction mixture. In a further stage, the reaction mixture is heated to a maximum of 350° C. and the remaining alkylated ($R_3M$) and partially alkylated products ($MCl_xR_y$, where x, y=1 or 2 and x+y=3) are separated off. These compounds can be recycled and used as starting materials in a further batch, so that a high metal utilization is ensured by the process of the invention.

The present invention makes a more rapid process possible, in particular in the preparation of trimethylgallium. The targeted use of inexpensive starting materials (for example alkylaluminium sesquichloride) enables the process to be carried out inexpensively on an industrial scale. Furthermore, the yields are significantly improved.

The trialkyl compounds of the type $R_3M$, preferably trimethylgallium, triethylgallium, trimethylindium and triethylindium, prepared according to the invention are suitable as precursors for metal organic chemical vapour deposition (MOCVD), a process which is widespread in, for example, the semiconductor and microelectronics industry.

Various processes for preparing trialkyl compounds of the type $R_3M$, in particular gallium alkyl compounds, are known in the prior art.

The reaction of gallium with dimethylmercury or diethylmercury is known. However, owing to the thermal instability of the higher mercury alkyls, the high toxicity of the mercury dialkyls and the extraordinarily slow reaction, this process is unsuitable for industrial use. Furthermore, the preparation can be effected by reaction of gallium trichloride with zinc dialkyls. However, the high spontaneous combustibility of the zinc dialkyls and the high light sensitivity of the higher alkyl derivatives greatly restrict the usability of this process.

The preparation from alkyl halides and gallium halides in the presence of sodium has also been found to be unsuitable because of possible impurities and reduction of the gallium halides used to metallic gallium.

Processes by means of which gallium alkyl and indium alkyl compounds are prepared by reaction of metal halides with Grignard reagent are likewise known. In this process, large amounts of salts are obtained, and these make complete reaction difficult and hinder the isolation of the trialkylgallium compounds and the yields are accordingly poor. In addition, the ethers used as solvent form stable adducts with the trialkylgallium compounds, and these are difficult to separate off.

Furthermore, processes by means of which gallium alkyl compounds are prepared from gallium halide and trialkylaluminium as alkylating reagent are known. Trialkylaluminium compounds are not toxic or light sensitive and are more thermally stable than corresponding mercury dialkyls or zinc dialkyls. In addition, known processes usually proceed in two or more stages since starting materials or the product produced have to be purified or isolated in a complicated manner. Furthermore, only small yields of gallium alkyl or indium alkyl compounds are frequently achieved by means of the known processes.

The processes known from the prior art normally take place in the presence of organic solvents in order to ensure reaction of the components and a quantitative conversion. However, this can result in organic impurities in the gallium alkyl compounds. This has a significant adverse effect on the purity of the gallium alkyl or indium alkyl compounds and thus their suitability as precursor for metal organic chemical vapour deposition processes (MOCVD). Thus, any impurities in the Ga-alkyl compound would have a significant adverse effect on the optical and electrical properties of the semiconductor layers (e.g. GaAs) produced using an MOCVD process.

Industrially, trimethylgallium (TMG) is at present usually prepared from gallium trichloride and an excess of trimethylaluminium as methylating reagent. The use of trimethylaluminium has the disadvantage that it has to be purified in a complicated manner before use as starting material, which makes the process for producing TMG expensive and time-consuming.

The U.S. Pat. No. 7,166,734 describes, inter alia, the preparation of trimethylgallium from gallium trichloride and trimethylaluminium in the presence of stoichiometric amounts of triethylamine in toluene as solvent.

Further, US 2006/0075959 A1 describes a process for preparing trimethylgallium using trimethylaluminium.

EP 1 489 085 A1, too, discloses the preparation of TMG by reaction of gallium trichloride with trimethylaluminium in organic solvents such as mesitylene or dichlorobenzene.

J. J. Eisch et al. describe a process for the preparation of triethylgallium and triisobutylgallium in hexane or pentane. Potassium chloride is added in a virtually equimolar ratio to triethylaluminium or triisobutylaluminium in order to complex the dialkylaluminium, so that gallium chloride can be alkylated further. The products are subsequently purified by redistillation over alkali metal fluorides in a further step (Eisch, J. J., *J. Amer. Chem. Soc.*, 1962, 84, 3605-3610).

Gaines et al., too, refer to the preparation of trimethylgallium from trimethylaluminium and also a subsequent distillation over sodium fluoride followed by redistillation. The yield is only about 63% (Gaines, D. F., Borlin, J., Fody, E. P., in: *Inorganic Syntheses*, 1974, 15, 203-207).

DE 1158 977 describes the reaction of gallium trichloride with trialkylaluminium or trialkylaluminium etherate. The trialkylgallium obtained is separated off by distillation and subsequently purified by rectification.

WO 00/37475 A1 discloses a continuous process for preparing TMG from trimethylaluminium and gallium trichloride in toluene.

EP1303336, too, describes a continuous process for preparing metal-organic compounds.

Starowieyski et al. describe the preparation of TMG from gallium trichloride and dimethylaluminium chloride in the presence of sodium chloride (Starowieyski K. B. et al, *Applied Organometallic Chemistry*, 2000, 14, 10, 616-622).

DE 40 05 726 A1 describes a process for preparing trialkylgallium compounds using alkylaluminium halides and in the presence of alkaline earth metal or alkali metal chlorides as auxiliary bases forming a salt melt at the reaction temperature. DE 40 05 726 A1 refers to the use of alkylaluminium sesquichlorides ($R_3Al_2Cl_3$) for preparing gallium alkyl compounds. The process is carried out without recirculation (separator) of the partially alkylated products, and the yields of fully alkylated products are from 10 to 48% (direct yield).

It is an object of the present invention to provide an improved process which makes an inexpensive preparation of trialkyl compounds of the metals of group IIIA of the PTE possible. The process should preferably be suitable for preparing trimethylgallium, triethylgallium, trimethylindium, and triethylindium. It should particularly preferably be suitable for preparing trimethylgallium and triethylgallium. The process should be based on the use of industrially readily available starting materials and ensure high yields and a high efficiency in respect of the use of the expensive metal starting materials.

The object of the present invention is achieved by the subject matter according to the present claims. In particular, the object is achieved by an improved process which is, inter alia, characterized by the starting substances used (e.g. alkylaluminium sesquichlorides) and the particular way of carrying out the reaction using a separator.

The present invention provides a process for preparing trialkylmetal compounds of the general formula $$R_3M$$

where
M=metal of group IIIA of the Periodic Table of the Elements (PTE)
R=$C_1$-$C_5$-alkyl, preferably methyl or ethyl,
which comprises the steps:
a) reaction of metal trichloride ($MCl_3$) with alkylaluminium sesquichloride ($R_3Al_2Cl_3$) in the presence of at least one alkali metal halide as auxiliary base,
b) heating of the reaction mixture to a temperature above 120° C. and separation of the trialkylmetal compound ($R_3M$) from the reaction mixture via a separator, with partially alkylated products of the type $MCl_xR_y$ (where x, y=1 or 2 and x+y=3) being recirculated to the reaction mixture,
c) heating of the reaction mixture to a temperature in the range from 165° C. to 350° C. and separation of the remaining trialkylmetal compound ($R_3M$) and the partially alkylated products ($MCl_xR_y$).
The process of the invention further comprises the step
d) re-use of the trialkylmetal compound ($R_3M$) obtained in step c) and the partially alkylated products $MCl_xR_y$ in the reaction mixture.

The process is based generally on the reaction of a metal trichloride ($MCl_3$ type) with an alkylating reagent. The reaction takes place in a reactor which is advantageously operated batchwise. However, a continuous process is also conceivable. For such continuous processes, specific flow reactors and/or microreactors may be employed. Suitable reactor types and process-relevant modifications are known to the person skilled in the art.

As an example, the process of the present invention is schematically depicted in FIG. 1 for a batchwise operation. Herein, the integers have the following meaning:
1=trialkylmetal compound $R_3M$
2=separator
3=partially alkylated metal compounds $MCl_xR_y$
4=reaction mixture (T>120° C.)

The reaction preferably proceeds in an inert gas atmosphere (argon or nitrogen). The reaction is preferably carried out under atmospheric pressure (=1+−0.2 bar). However, depending on the boiling point of the alkylmetal compound, a moderate vacuum (down to 0.001 bar) may also be applied.

As alkylating reagents, use is made of alkylaluminium sesquichlorides, preferably methylaluminium sesquichloride ($Me_3Al_2Cl_3$) and ethylaluminium sesquichloride ($Et_3Al_2Cl_3$). These starting materials have the advantage that they are formed as intermediates in the preparation of trimethylaluminium or triethylaluminium and do not require complicated purification. Such products are commercially available from various manufacturers (for example from Chemtura Organometallics GmbH, Bergkamen, DE). The use of these alkylating reagents thus makes a more inexpensive and resource-sparing preparation possible compared to the conventional use of trimethylaluminium as starting material. It has surprisingly been found that, for example when using methylaluminium sesquichloride as methylating reagent in the process of the invention, high crude yields of TMG can be achieved.

In the preparation of the trialkylmetal compounds, preference is given to using from 1 to 10 equivalents of alkylaluminium sesquichloride per equivalent of metal trichloride. Further preference is given to using from 1 to 4 equivalents and particularly preferably from 1 to 2 equivalents of alkylaluminium sesquichloride per equivalent of metal trichloride. In a particularly preferred embodiment, 3 equivalents of alkylaluminium sesquichloride are used per equivalent of metal trichloride. In this way, particularly high yields of trialkylmetal compounds can be achieved. The term "equivalent" as used in the present patent application refers to the molar ratios based on the molar amounts of the starting materials.

The reaction takes place in the presence of at least one auxiliary base. The auxiliary base comprises at least one alkali metal halide, preferably at least one alkali metal chloride. Further preference is given to the alkali metal chlorides sodium chloride (NaCl) and potassium chloride (KCl) and mixtures thereof since these salts together with the Al-containing reaction products, in particular $AlCl_3$, form a salt melt which is liquid at the reaction temperature. The use of additional organic solvents can therefore be dispensed with.

The alkali metal chloride is preferably water-free. For the purposes of the present invention, water-free means a water content of <10 ppm, more preferably <8 ppm and particularly preferably <5 ppm. A water content of >10 ppm can lead to secondary reactions and reduce the yield of trialkylmetal compound.

The auxiliary base particularly preferably comprises a mixture of potassium chloride and sodium chloride in which the molar ratio of sodium chloride to potassium chloride is in the range from 6:4 to 8:2, more preferably from 6:3 to 8:3 and particularly preferably from 6.5:3 to 7.5:3. Adherence to such a molar ratio surprisingly leads to particularly high yields of TMG despite the high proportion of sodium. In a particularly preferred embodiment, the molar ratio of sodium chloride to potassium chloride is 7:3.

The ratio of equivalents of the sum of sodium chloride and potassium chloride used to the number of equivalents of the alkylating reagent used is preferably from 1.5:1 to 2.5:1, more preferably from 1.75:1 to 2.25:1. In a particularly preferred embodiment, the ratio of the equivalents of the sum of sodium chloride and potassium chloride used to the number of equivalents of the methylating reagent used is 2:1. This makes it possible to prepare the trialkylmetal compounds in a particularly high yield.

In the preparation of the trialkylmetal compounds, the introduction of the starting materials, for example gallium trichloride and methylaluminium sesquichloride ($Me_3Al_2Cl_3$), into the reactor is preferably time offset. Particular preference is given to a mixture comprising metal trichloride and auxiliary base firstly being placed in the reactor and alkylaluminium sesquichloride subsequently being added with a time offset to this mixture. This leads to high yields and also simplifies the outlay in terms of apparatus. Thus, the auxiliary base and the metal halide can simply be weighed into the reactor.

Auxiliary base and gallium halide are preferably present in the solid state. Controlled addition of the liquid alkylating reagent can subsequently be carried out. The addition of the alkylating reagent to the mixture of metal trichloride and auxiliary base is generally carried out via a dropping funnel. The addition of the alkylating reagent is preferably carried out with stirring of the mixture of metal halide and auxiliary base in order to ensure satisfactory mixing and quantitative conversion.

The temperature during the addition of the alkylating reagent is preferably below 130° C. Particular preference is given to a temperature of 130° C. not being exceeded during the addition of the alkylating reagent in order to avoid undesirable secondary reactions. Since the reaction is strongly exothermic, it is preferably controlled via the speed of addition and the partial amounts of the alkylating reagent which are added in each case.

In a variant of the process, a mixture comprising metal trichloride and auxiliary base is initially charged and alkylaluminium sesquichloride ($R_3Al_2Cl_3$) is subsequently added to this mixture with a time offset in step a).

In another variant, a mixture comprising alkylaluminium sesquichloride ($R_3Al_2Cl_3$) and auxiliary base is initially charged and metal trichloride is subsequently added to this mixture with a time offset in step a).

After the reaction of the metal chloride with the alkylating reagent, the reaction mixture is heated to a temperature above 120° C., preferably above 130° C., and the trialkylmetal compound ($R_3M$) is separated off from the reaction mixture. This separation is not quantitative; it preferably serves to remove the reaction product from the reaction mixture and thus shift the equilibrium in the direction of the reaction products.

The separation from the reaction mixture is effected via a separator installed on the reactor, with partially alkylated products of the type $MCl_xR_y$ (where x, y=1 or 2 and x+y=3) at the same time being recirculated to the reaction mixture. As a result, these compounds are alkylated further and a higher direct yield of trialkylmetal compound ($R_3M$) is surprisingly achieved.

This separation is not quantitative; it preferably serves to recirculate the partially alkylated products to the reaction mixture in order to complete alkylation. In addition, the removal of the reaction product (trialkylmetal compound $R_3M$) from the reaction mixture shifts the equilibrium in the direction of the reaction products.

Regarding the preparation of trialkylgallium compounds, the process of the invention differs from the process previously disclosed in DE 40 05 726 in a modified way of carrying out the reaction and in particular in the use of a "separator". The use of this separator according to the invention surprisingly enables the desired trialkylgallium compound to be obtained in a significantly higher direct yield under comparable reaction conditions.

Thus, for example, in the case of trimethylgallium a direct yield of 68% is achieved by means of the process described here with the use of the separator and use of equivalent amounts of the starting materials ($GaCl_3/Me_3Al_2Cl_3$=1/1), while a yield of only 25.6% trimethylgallium is obtained as reported in DE 40 05 726 (example 4) with a comparable batch. When duplicating example 4 of DE 40 05 726, the inventors found a yield of 21.3% trimethylgallium (ref to Comparative Example CE2).

To give a better understanding, the reaction stepss proceeding during the process will be illustrated below for the example of the preparation of trimethylgallium by reaction of $GaCl_3$ with $Me_3Al_2Cl_3$. In principle, the following reaction occurs:

$$GaCl_3+Me_3Al_2Cl_3+2Na/KCl \rightarrow Me_3Ga+2Na/KAlCl_4 \quad (1)$$

However, the reaction equation (1) indicates the way in which the reaction proceeds only imprecisely and incompletely. Thus, direct transfer of all methyl groups from aluminium to gallium cannot be observed, but instead only a partial alkylation in which dimethyl gallium chloride ($Me_2GaCl$) is formed; cf. equation (2), initially takes place at temperatures below 120° C.:

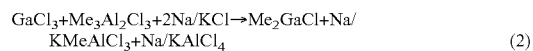

$$GaCl_3+Me_3Al_2Cl_3+2Na/KCl \rightarrow Me_2GaCl+Na/KMeAlCl_3+Na/KAlCl_4 \quad (2)$$

The occurrence of the monomethylated species methylgallium dichloride ($MeGaCl_2$) can, on the other hand, generally not be observed. When the reaction melt is heated to temperatures above 120° C., preferably above 125° C., the partially alkylated species is then alkylated further by the alkyl groups still present in the reaction melt to form trimethylgallium; cf. equation (3):

$$Me_2GaCl+Na/KMeAlCl_3 \rightarrow Me_3Ga+Na/KAlCl_4 \quad (3)$$

Without this heating of the reaction mixture, the second alkylation step does not take place and only $Me_2GaCl$ can be isolated as product immediately after the addition of $GaCl_3$ to the $Me_3Al_2Cl_3$.

During heating, too, mainly dimethylgallium chloride and only small amounts of the trimethylgallium being formed consequently occur in the reaction melt. As a result of the high temperatures prevailing during heating, the trimethylgallium formed is immediately distilled off from the reaction melt.

However, since the formation and liberation of trimethylgallium takes place only in a temperature range in which the boiling range of the major partially alkylated species dimethylgallium chloride ($Me_2GaCl$, b.p. 167-168° C.) is likewise located, a mixture of completely and partially alkylated products will always be isolated in the process described in DE 40 05 726.

With the use of a separator operated in a suitable temperature range according to the present invention, it is possible to isolate the desired trialkylmetal compounds without simultaneous separation of the partially alkylated species from the reaction mixture. As a result of the recirculation (effected by means of a separator) of the partially alkylated compound into the reaction mixture, this is advantageously subjected to a further alkylation as per equation (3), so that the achievable yields of trialkylmetal compounds can be significantly increased.

On the laboratory scale, the reaction can be carried out in a 4-neck flask provided with stirrer, dropping funnel, a separator and a further outlet. Corresponding pilot plants can, for example, be constructed in stainless steel.

The trialkylmetal compound ($R_3M$) formed in reaction step a) is isolated from the residual mixture remaining in the reactor. The isolation is preferably carried out by distillation using a separator which in principle represents a heated separation element. For example, a heated packed column or a heated reflux condenser can be used on the laboratory scale. On the pilot plant scale or in industrial production, appropriately dimensioned industrial embodiments should be used.

The separator is generally operated at atmospheric pressure ($1\pm0.2$ bar) and heated to a temperature which is from 5 to 40° C. above, preferably from 10 to 25° C. above, the boiling point of the trialkylmetal compound $R_3M$ formed in the reaction mixture.

Furthermore, the separator is, according to the invention, heated to a temperature which is more than 30° C. below, preferably more than 60° C. below, the boiling point of the most volatile partially alkylated metal compounds $MCl_xR_y$ (where x, y=1 or 2 and x+y=3) formed in the reaction mixture.

In the case of TMG (boiling point about 56° C.), the separator is heated to a temperature in the range from 60 to 90° C., preferably to a temperature in the range from 70 to 80° C. It is particularly preferably operated at about 70° C. This temperature is 14° C. above the boiling point of TMG and 98° C. below the boiling point of dimethylgallium chloride (b.p. 168° C.). The isolation by distillation via the separator is preferably carried out under atmospheric pressure.

In the case of triethylgallium (TEG, b.p. 143° C.), the separator is heated to a temperature in the range from 150 to 180° C., preferably to a temperature in the range from 155 to 170° C. when carrying out the process at atmospheric pressure ($1\pm0.2$ bar).

However, for the preparation of triethylgallium, the process of the invention is preferably carried out under reduced pressure in step b) and the temperature of the separator is adapted to the reduced boiling point of the partially alkylated product. Thus, the boiling point of diethylgallium chloride is 60-62° C. (at 3 mbar).

For the preparation of TEG, a separator temperature in the range from 100 to 160° C., preferably in the range from 120 to 150° C., at a reduced pressure in the range to 1 mbar ($10^{-3}$ bar) has been found to be useful in the process of the invention.

After the isolation in step b) of the process of the invention is concluded, the reaction mixture is in step c), heated further to a temperature in the range from 165° C. to 350° C., preferably to a temperature in the range from 180° C. to 300° C. Here, the remaining trialkylmetal compound ($R_3M$) and the partially alkylated products ($MCl_xR_y$) are separated off from the reaction mixture. This isolation, too, is preferably carried out by distillation with application of a reduced pressure. Preference is given to selecting a fine to high vacuum in the range from $10^{-1}$ to $10^{-4}$ mbar. The reduced pressure makes it possible to use comparatively low temperatures, so that an inexpensive process is possible. The isolation of the residue is preferably effected via a separate outlet on the reactor.

In a preferred variant of the process, the trialkylmetal compounds ($R_3M$) and the partially alkylated products ($MCl_xR_y$) isolated by the separation in step c) are re-used in a subsequent batch and added to the fresh reaction mixture (cf. step d) of the process of the invention).

If an excess of alkylating reagent ($\geq 3$ equivalents of alkylaluminium sesquichloride) is employed, reuse as per step d) can be dispensed with and the reaction product from step c) can be passed directly to fine purification. This optional recycling of the expensive metal compounds makes the process of the invention particularly economical. In addition, for example in the case of TMG, the gallium utilization and the TMG yield can be increased further.

According to the invention, a salt melt which is liquid at the reaction temperature preferably remains as residual mixture after carrying out steps a) to c). In general, no pyrophoric alkyl metal compounds remain in the residual mixture. This has the advantage that complicated and costly disposal is dispensed with. The residual mixture particularly preferably comprises compounds selected from among Na/K[$AlCl_4$], Na/K[$MeAlCl_3$] and mixtures thereof.

In the case of TMG, direct yields in the range from 60 to 90% can surprisingly be achieved by means of the process of the invention. For the purposes of the present invention, the direct yield or "crude yield" is the yield after step b) of the process. The trialkylmetal compounds obtained in the direct yield generally still contain from 0.1 to 1% by weight of the dimethylated products (measured by means of $^1$H-NMR).

Thus, in a further preferred variant of the process, the heating step c) is optional and may be dispensed with. In such case, the direct yield or "crude yield" of trialkyl metal compound after step b) is obtained.

To calculate the total yield, the trialkylmetal compounds obtained in step c) of the process are added thereto. Total yields of up to 99% (in the case of TMG, based on Ga) are then obtained.

The trialkylmetal compounds obtained in steps b) and optionally c) of the process are generally subjected to a fine purification in a subsequent step. This is generally a rectification and/or a distillation, optionally in a plurality of steps. Highly pure trialkylmetal compounds which meet the requirements of the MOCVD industry are obtained in this way The trialkylmetal compounds, in particular trimethylgallium (TMG) or triethylgallium (TEG), prepared by the process of the invention are particularly suitable as metal organic precursor for metal organic chemical vapour deposition (MOCVD), for example for producing semiconductor layers composed of GaAs. The semiconductor layers (III/V semiconductors, etc.) ultimately produced therefrom have a variety of industrial uses.

The invention is now explained in more detail by the following examples, which are considered illustrative, but do not limit the scope of the invention and the resulting claims.

EXAMPLES

General

The products and the sesquichlorides used in the synthesis are pyrophoric. All work is therefore carried out with rigorous exclusion of air and moisture under protective gas (argon, nitrogen).

Example 1

Preparation of Trimethylgallium (TMG)

200.0 g (1.14 mol) of $GaCl_3$ (high-purity, MCP Group, Tilly, BE), 92.9 g (1.59 mol, 1.4 equivalents) of dry NaCl (Merck, water content <5 ppm) and 50.8 g (0.68 mol, 0.6 equivalent) of dry KCl (Merck, water content <5 ppm) are placed under inert gas (argon, purity 6.0) in a 500 ml 4-necked flask provided with stirrer, dropping funnel and a packed column maintained at 70° C. as separator and also a further outlet.

While stirring, 233.5 g (1.14 mol, 1 equivalent) of methylaluminium sesquichloride ($Me_3Al_2Cl_3$, Chemtura Organometallics GmbH, Bergkamen, DE) are added in such a way that the temperature in the reaction mixture does not exceed 130° C. The ratio of equivalents of $GaCl_3$ to $Me_3Al_2Cl_3$ is 1:1.

During the subsequent heating up, $Me_3Ga$ can be isolated above 155° C. When the reaction temperature reaches 180° C., isolation of the product via the separator is stopped. This gives a total of 89.0 g of $Me_3Ga$ (corresponding to a direct yield of 68%). The $Me_3Ga$ present in the direct yield contains 0.5% by weight of $Me_2GaCl$ (measured by means of $^1$H-NMR).

A reduced pressure (to $10^{-3}$ mbar, oil pump) is applied and the remaining Ga-containing compounds (47 g, mixture of $Me_3Ga$ and $Me_2GaCl$) are removed from the reaction mixture via a second outlet. The total yield is 72.2% of $Me_3Ga$. Taking into account 27.4% of $Me_2GaCl$, the total conversion based on Ga is thus 99.6%. The $Me_3Ga$ present in the direct yield contains 0.5% by weight of $Me_2GaCl$ (measured by means of $^1$H-NMR). The mixture of $Me_3Ga$ and $Me_2GaCl$ is reused in other batches (cf. Example 2).

Example 2

(TMG, with Re-Use)

183.1 g (1.04 mol) of $GaCl_3$, 92.9 g (1.59 mol) of dry NaCl, 50.8 g (0.68 mol) of dry KCl and also 40.4 g (0.3 mol) of $Me_2GaCl$ and 5.5 g (0.05 mol) of $Me_3Ga$ (isolated mixture from Example 1) are placed under inert gas (argon, purity 6.0) in a 500 ml 4-neck flask provided with stirrer, dropping funnel and a packed column maintained at 70° C. as separator and also a further outlet.

While stirring, 233 g (1.14 mol) of $Me_3Al_2Cl_3$ are added in such a way that the temperature in the reaction mixture does not exceed 130° C. During subsequent heating up, $Me_3Ga$ is isolated above 155° C. (99.3 g, corresponding to a direct yield of 61.7%).

When the reaction temperature reaches 180° C., the isolation of the product via the separator is stopped and the remaining Ga-containing compounds (residue) are isolated from the residual mixture via the second outlet with application of a reduced pressure (70.0 g, mixture of $Me_3Ga$ and $Me_2GaCl$). The total yield is 64.0% of $Me_3Ga$. Taking into account 35.8% of $Me_2GaCl$, the total conversion (based on Ga) is 99.8%. The isolated crude $Me_3Ga$ from the direct yield contains 0.8% by weight of $Me_2GaCl$ (measured by means of $^1$H-NMR). The mixture of $Me_3Ga$ and $Me_2GaCl$ is recirculated as starting material instead of $GaCl_3$ in a further pass.

Example 3

(TMG, Ratio of Equivalents 1:3)

45.0 g (0.26 mol) of $GaCl_3$, 62.7 g (1.07 mol, 4.2 equivalents) of dry NaCl and 34.3 g (0.46 mol, 1.8 equivalents) of dry KCl are placed under argon in a 500 ml 4-neck flask provided with stirrer, dropping funnel and a packed column maintained at 70° C. as separator.

While stirring, 162.8 g (0.79 mol, 3 equivalents) of $Me_3Al_2Cl_3$ are added in such a way that the temperature in the reaction mixture does not exceed 130° C. During subsequent heating up, $Me_3Ga$ is isolated above 155° C. (26.6 g; corresponding to a direct yield of 88% of crude TMG).

When the reaction temperature reaches 180° C., the isolation of the product via the separator is stopped and the remaining Ga-containing compounds are removed from the residual mixture via a second outlet with application of a reduced pressure (6.9 g). In total, 99.0% of $Me_3Ga$ and 0.9% of $Me_2GaCl$ are isolated, and the total conversion (based on Ga) is 99.9%. The isolated crude TMG contains 0.7% by weight of $Me_2GaCl$ and 1.4% by weight of $Me_2AlCl$ (measured by means of $^1$H-NMR).

Example 4

(Preparation of Triethylgallium, TEG)

200.0 g (1.14 mol) of $GaCl_3$, 92.9 g (1.59 mol, 1.4 equivalents) of dry NaCl (water content <5 ppm) and 50.8 g (0.7 mol, 0.6 equivalent) of dry KCl (water content <5 ppm) are placed under inert gas (argon) in a 500 ml 4-neck flask provided with stirrer, dropping funnel and a packed column maintained at 160° C. as separator.

While stirring, 282.0 g (1.14 mol, 1 equivalent) of ethylaluminium sesquichloride ($Et_3Al_2Cl_3$) are added in such a way that the temperature in the reaction mixture does not exceed 130° C. During subsequent heating up, $Et_3Ga$ can be isolated. When the reaction temperature reaches 250° C., the isolation of the product via the separator is stopped and the remaining Ga-containing compounds (mixture of $Et_3Ga$ and $Et_2GaCl$) are removed from the reaction mixture via a second outlet with application of a reduced pressure.

Example 5

(Preparation of triethylgallium (TEG, Reduced Pressure)

68.9 g (0.39 mol) of $GaCl_3$, 32.0 g (0.55 mol, 1.4 equivalents) of dry NaCl and 17.5 g (0.23 mol, 0.6 equivalent) of dry KCl are placed under argon in a 500 ml four-neck flask provided with stirrer, dropping funnel and a separator maintained at 130° C.

While stirring, 120.2 g (0.47 mol, 1.2 equivalents) of ethylaluminium sesquichloride ($Et_3Al_2Cl_3$) are added in such a way that the temperature in the reaction mixture does not exceed 120° C. The reaction mixture is subsequently heated while applying a reduced pressure of 300 mbar, and $Et_3Ga$ is thus isolated (46.6 g; direct yield 75.9%). After the isolation of the product via the separator is complete, the remaining gallium-containing compounds are removed from the reaction mixture via a second outlet under a high vacuum (to $10^{-3}$ mbar) (14.6 g, mixture of $Et_3Ga$ and $Et_2GaCl$).

In total, 80.9% of $Et_3Ga$ and 19% of $Et_2GaCl$ are isolated, and the total yield (based on Ga) is 99.9%. The isolated crude $Et_3Ga$ contains 2.6% by weight of $Et_2GaCl$ (measured by means of $^1$H-NMR).

Example 6

(TMG, Ratio of Equivalents 1:1.5)

170 g (0.97 mol) of $GaCl_3$, 118.5 g (2.03 mol, 2.1 equivalents) of dry NaCl and 64.9 g (0.87 mol, 0.9 equivalent) of dry KCl are placed under argon in a 500 ml 4-neck flask provided with stirrer, dropping funnel and a packed column maintained at 70° C. as separator.

While stirring, 289.1 g (1.45 mol, 1.5 equivalents) of $Me_3Al_2Cl_3$ are added in such a way that the temperature in the reaction mixture does not exceed 130° C. During subsequent heating up, $Me_3Ga$ is isolated above 155° C. (97.8 g; direct yield 87%). When the reaction temperature reaches 180° C., the isolation of the product via the separator is stopped and the remaining Ga-containing compounds are removed from the residual mixture via a second outlet with application of a reduced pressure (14.8 g, mixture of Me₃Ga and Me₂GaCl). The direct yield of TMG is 87%. In total, 95.6% of TMG and 4% of Me₂GaCl are isolated, corresponding to a Ga utilization of 99.6%. The isolated crude TMG contains 0.7% by weight of Me₂GaCl as impurity ($^1$H-NMR).

Comparative Example CE1

(TMG, without Use of a Separator)

The experimental conditions are identical to Example 6, but the experiment is carried out without use of a separator.

170 g (0.97 mol) of GaCl₃, 118.5 g (2.03 mol, 2.1 equivalents) of dry NaCl and 64.9 g (0.87 mol, 0.9 equivalents) of dry KCl are placed under argon in a 500 ml 4-neck flask provided with stirrer, dropping funnel and a distillation attachment.

While stirring, 289.1 g (1.45 mol, 1.5 equivalents) of Me₃Al₂Cl₃ are added in such a way that the temperature in the reaction mixture does not exceed 130° C. During subsequent heating up of the reaction mixture, liquid distils over above a temperature of 150° C. The overhead temperature measured at the distillation attachment is 63° C. at this point in time. When no more liquid goes over, the distillation is stopped at a temperature of 250° C. in the reaction mixture. 104.6 g of a product mixture which is partly solid at room temperature and consists of 74.5% of Me₃Ga and 16.3% of Me₂GaCl (determined by means of $^1$H-NMR) are isolated. The direct yield of TMG is thus about 12.5% lower than in Example 6. In addition, the TMG obtained is highly contaminated with the partially methylated product.

Comparative Example CE2

(TMG, According to DE 40 05 726, Example 4)

A 500 ml 4-neck flask equipped with stirrer, thermocouple and dropping funnel is charged with GaCl₃ (50.0 g, 0.28 mol) and methylaluminum sesquichloride (58.3 g, 0.28 mol, 1 equivalent) is added dropwise via the dropping funnel. After the reaction mixture has cooled to room temperature the flask is transferred to a glovebox and dry NaCl (23.2 g, 0.40 mol, 1.4 equivalents) and dry KCl (12.7 g, 0.17 mol, 0.6 equivalent) are added. The dropping funnel is replaced with a CLAISEN head with attached cold-trap. The apparatus is taken out of the glovebox and the reaction mixture is slowly heated under constant stirring to 350° C. At a temperature between 100 and 120° C. the reaction mixture becomes liquid; between 155 and 160° C. a clear liquid starts to distill off and is collected in an ice-cooled cold-trap. The collected product, at room temperature partially solid, overall 36.9 g, is identified by means of NMR as a mixture of Me₃Ga and Me₂GaCl, containing 21.3% Me₃Ga and 78.7% Me₂GaCl.

Example 7

Preparation of trimethylindium (TMI)

A 250 ml 4-neck flask equipped with stirrer, thermocouple, dropping funnel and separator with an attached cold-trap is charged in a glovebox with InCl₃ (10.0 g, 45.2 mmol), dry NaCl (3.67 g, 63.3 mmol, 1.40 equivalents) and dry KCl (2.02 g, 27.1 mmol, 0.6 equivalents) and the dropping funnel is charged with methylaluminum sesquichloride (9.29 g, 45.2 mmol, 1.0 equivalent). The apparatus is transferred out of the glovebox and methylaluminum sesquichloride is added to the salt mixture. The reaction mixture is then slowly heated to 150° C. under constant stirring with the temperature of the separator set to 80° C. When the reaction mixture is completely liquid, the cold-trap is cooled with liquid nitrogen and by applying a vacuum (10⁻³ mbar) to the apparatus, trimethylindium is sublimed into the cold-trap. When all trimethylindium is sublimed out of the reaction flask the product isolation via the separator is stopped, a new cold-trap is attached directly to the reaction flask and the remaining dimethylindium chloride in the reaction mixture is sublimed out by raising the temperature up to 250° C.

The invention claimed is:

1. A process for preparing trialkylmetal compounds of the general formula $$R_3M$$

where
   M=metal of group IIIA of the Periodic Table of the Elements (PTE)
   R=C₁-C₅-alkyl,
which comprises the steps:
   a) reaction of metal trichloride (MCl₃) with alkylaluminium sesquichloride (R₃Al₂Cl₃) in the presence of at least one alkali metal halide as auxiliary base,
   b) heating of the reaction mixture to a temperature above 120° C. and separation of the trialkylmetal compound (R₃M) from the reaction mixture via a separator, with partially alkylated products of the type MCl$_x$R$_y$ (where x, y=1 or 2 and x+y=3) being recirculated to the reaction mixture, wherein the separator is a heatable separation element and the separator is heated to a temperature which is from 5 to 40° C. above the boiling point of the trialkylmetal compound (R₃M) formed in the reaction mixture, and
   c) heating of the reaction mixture to a temperature in the range from 165° C. to 350° C. and separation of the remaining trialkylmetal compound (R₃M) and the partially alkylated products (MCl$_x$R$_y$) from the reaction mixture.

2. The process according to claim 1 which further comprises the step
   d) re-use of the trialkylmetal compound (R₃M) obtained in step c) and the partially alkylated products (MCl$_x$R$_y$) in the reaction mixture.

3. The process according to claim 1, which further comprises the fine purification of the trialkylmetal compound in a subsequent step.

4. The process according to claim 1, wherein gallium (Ga) or indium (In) is used as the metal of group IIIA of the PTE.

5. The process according to claim 1, wherein the alkyl group R is a methyl or ethyl group.

6. The process according to claim 1, wherein R₃M is trimethylgallium.

7. The process according to claim 1, wherein R₃M is triethylgallium.

8. The process according to claim 1, wherein R₃M is trimethylindium.

9. The process according to claim 1, wherein R₃M is triethylindium.

10. The process according to claim 1, wherein the separation of the remaining trialkylmetal compound (R₃M) and the partially alkylated products from the reaction mixture in step c) is carried out under reduced pressure.

11. The process according to claim 1, wherein methylaluminium sesquichloride [(CH₃)₃Al₂Cl₃] or ethylaluminium sesquichloride [(C₂H₅)₃Al₂Cl₃] is used as alkylaluminium sesquichloride.

12. The process according to claim 1, wherein the separator is a heated packed column.

13. The process according to claim 1, wherein the separator is operated at atmospheric pressure (1±0.2 bar) and is heated to a temperature which is from 10 to 25° C. above the boiling point of the trialkylmetal compound $R_3M$ formed in the reaction mixture.

14. The process according to claim 1, wherein the separator is operated at atmospheric pressure (1±0.2 bar) and is heated to a temperature which is more than 30° C. below the boiling point of the most volatile partially alkylated metal compound $MCl_xR_y$ (where x, y=1 or 2 and x+y=3) formed in the reaction mixture.

15. The process according to claim 13, wherein $R_3M$ is trimethylgallium and the separator is heated to a temperature in the range from 60 to 90° C.

16. The process according to claim 13, wherein $R_3M$ is triethylgallium and the separator is heated to a temperature in the range from 150 to 180° C.

17. The process according to claim 1, wherein $R_3M$ is triethylgallium and the separator is operated at a reduced pressure up to $10^{-3}$ bar and is heated to a temperature in the range from 100 to 160° C.

18. The process according to claim 1, wherein the auxiliary base in step a) is a mixture of sodium chloride and potassium chloride and the molar ratio of sodium chloride to potassium chloride is in the range from 6:3 to 8:3.

19. The process according to claim 1, wherein a salt melt which is liquid at the reaction temperature is formed by the auxiliary base in step a) in combination with the Al-containing reaction products.

20. The process according to claim 1, wherein 1.5 to 2.5 equivalents of auxiliary base per equivalent of alkylaluminium sesquichloride ($R_3Al_2Cl_3$) are used in step a).

21. The process according to claim 1, wherein 1 to 10 equivalents of alkylaluminium sesquichloride ($R_3Al_2Cl_3$) per equivalent of metal trichloride are used in step a).

22. The process according to claim 1, wherein 3 equivalents of alkylaluminium sesquichloride ($R_3Al_2Cl_3$) per equivalent of metal trichloride are used in step a).

23. The process according to claim 1, wherein the starting materials metal trichloride and alkylaluminium sesquichloride ($R_3Al_2Cl$) are introduced into the reactor with a time offset in step a).

24. The process according to claim 1, wherein, in step a), a mixture comprising metal trichloride and auxiliary base is initially charged and alkylaluminium sesquichloride ($R_3Al_2Cl_3$) is subsequently added to this mixture with a time offset.

25. The process according to claim 1, wherein, in step a), a mixture comprising alkylaluminium sesquichloride ($R_3Al_2Cl_3$) and auxiliary base is initially charged and metal trichloride is subsequently added to this mixture with a time offset.

26. The process according to claim 1, said process being carried out in a continuous process.

27. The process of claim 3, wherein the fine purification is a rectification and/or a distillation.

28. The process of claim 4, wherein gallium (Ga) is used as the metal of group IIIA of the PTE.

29. The process of claim 5, wherein the alkyl group R is a methyl group.

30. The process of claim 14, wherein the separator is heated to a temperature which is more than 60° C. below the boiling point of the most volatile partially alkylated metal compound $MCl_xR_y$ (where x, y=1 or 2 and x+y=3) formed in the reaction mixture.

31. The process of claim 15, wherein the separator is heated to a temperature in the range from 70 to 80° C.

32. The process of claim 16, wherein the separator is heated to a temperature in the range from 155 to 170° C.

33. The process of claim 17, wherein the separator is heated to a temperature in the range from 100 to 150° C.

34. The process of claim 19, wherein a salt melt which is liquid at the reaction temperature is formed by the auxiliary base in step a) in combination with $AlCl_3$.

35. The process of claim 21, wherein 1 to 4 equivalents of alkylaluminium sesquichloride ($R_3Al_2Cl_3$) per equivalent of metal trichloride are used in step a).

36. The process of claim 35, wherein 1 to 2 equivalents of alkylaluminium sesquichloride ($R_3Al_2Cl_3$) per equivalent of metal trichloride are used in step a).

37. A process for preparing trialkylmetal compounds of the general formula $$R_3M$$

where
M=metal of group IIIA of the Periodic Table of the Elements (PTE)
R=$C_1$-$C_5$-alkyl,
which comprises the steps:
a) reaction of metal trichloride ($MCl_3$) with alkylaluminium sesquichloride ($R_3Al_2Cl_3$) in the presence of at least one alkali metal halide as auxiliary base,
b) heating of the reaction mixture to a temperature above 120° C. and separation of the trialkylmetal compound ($R_3M$) from the reaction mixture via a separator, with partially alkylated products of the type $MCl_xR_y$ (where x, y=1 or 2 and x+y=3) being recirculated to the reaction mixture, wherein the separator is a heated packed column or a heated reflux condenser, and
c) heating of the reaction mixture to a temperature in the range from 165° C. to 350° C. and separation of the remaining trialkylmetal compound ($R_3M$) and the partially alkylated products ($MCl_xR_y$) from the reaction mixture.

38. A process for preparing trialkylmetal compounds of the general formula $$R_3M$$

where
M=metal of group IIIA of the Periodic Table of the Elements (PTE)
R=$C_1$-$C_5$-alkyl,
which comprises the steps:
a) reaction of metal trichloride ($MCl_3$) with alkylaluminium sesquichloride ($R_3Al_2Cl_3$) in the presence of at least one alkali metal halide as auxiliary base,
b) heating of the reaction mixture to a temperature above 120° C. and separation of the trialkylmetal compound ($R_3M$) from the reaction mixture via a separator, with partially alkylated products of the type $MCl_xR_y$ (where x, y=1 or 2 and x+y=3) being recirculated to the reaction mixture, wherein the separator is a heatable separation element and the separator is heated to a temperature which is more than 30° C. below the boiling point of the most volatile partially alkylated metal compound $MCl_xR_y$ (where x, y=1 or 2 and x+y=3) formed in the reaction mixture, and
c) heating of the reaction mixture to a temperature in the range from 165° C. to 350° C. and separation of the remaining trialkylmetal compound ($R_3M$) and the partially alkylated products ($MCl_xR_y$) from the reaction mixture.

39. The process of claim 38, wherein the separator is operated at atmospheric pressure (1±0.2 bar) and is heated to a temperature which is more than 60° C. below the boiling point of the most volatile partially alkylated metal compound $MCl_xR_y$ (where x, y=1 or 2 and x+y=3) formed in the reaction mixture.

40. The process of claim 1, wherein the separator is operated at atmospheric pressure (1±0.2 bar).

41. The process of claim 38, wherein the separator is operated at atmospheric pressure (1±0.2 bar).

42. A process for preparing trialkylmetal compounds of the general formula $$R_3M$$

where
M=metal of group IIIA of the Periodic Table of the Elements (PTE)
R=$C_1$-$C_5$-alkyl,
which comprises the steps:
a) reaction of metal trichloride ($MCl_3$) with alkylaluminium sesquichloride ($R_3Al_2Cl_3$) in the presence of at least one alkali metal halide as auxiliary base,
b) heating of the reaction mixture to a temperature above 120° C. and separation of the trialkylmetal compound ($R_3M$) from the reaction mixture via a separator, with partially alkylated products of the type $MCl_xR_y$ (where x, y=1 or 2 and x+y=3) being recirculated to the reaction mixture, wherein the separator is a heatable separation element, and
c) heating of the reaction mixture to a temperature in the range from 165° C. to 350° C. and separation of the remaining trialkylmetal compound ($R_3M$) and the partially alkylated products ($MCl_xR_y$) from the reaction mixture, and
wherein the heating of the separator is carried out at a level that provides for a direct yield of the trialkylmetal compound ($R_3M$) of at least 64 percent under the process.

43. The process of claim 42, wherein the separator is heated to a temperature which is from 5 to 40° C. above the boiling point of the trialkylmetal compound ($R_3M$) formed in the reaction mixture and which is more than 30° C. below the boiling point of the most volatile partially alkylated metal compound $MCl_xR_y$ (where x, y=1 or 2 and x+y=3) formed in the reaction mixture.

44. The process of claim 43, wherein the separator is operated at atmospheric pressure (1±0.2 bar).

45. The process of claim 42, wherein the direct yield of the trialkylmetal compound ($R_3M$) is about 64 percent to about 88 percent under the process.

\* \* \* \* \*